US009226897B2

(12) United States Patent
De Rosa et al.

(10) Patent No.: US 9,226,897 B2
(45) Date of Patent: Jan. 5, 2016

(54) SELF-ASSEMBLING NANOPARTICLES FOR THE RELEASE OF BISPHOSPHONATES IN THE TREATMENT OF HUMAN CANCERS

(75) Inventors: Giuseppe De Rosa, Naples (IT); Michele Caraglia, Ariano Irpino (IT); Pierfrancesco Tassone, Catanzaro (IT); Maria Immacolata La Rotonda, Naples (IT); Alberto Abbruzzese Saccardi, Naples (IT); Giuseppina Salzano, Casavatore (IT); Monica Marra, Naples (IT); Carlo Leonetti, Rome (IT)

(73) Assignee: Istituti Fisioterapici Ospitalieri, Rome (IT)

( * ) Notice: Subject to any disclaimer, the term of this patent is extended or adjusted under 35 U.S.C. 154(b) by 0 days.

(21) Appl. No.: 13/876,581

(22) PCT Filed: Sep. 30, 2011

(86) PCT No.: PCT/EP2011/067119
§ 371 (c)(1),
(2), (4) Date: Jul. 31, 2013

(87) PCT Pub. No.: WO2012/042024
PCT Pub. Date: Apr. 5, 2012

(65) Prior Publication Data
US 2014/0086979 A1 Mar. 27, 2014

(30) Foreign Application Priority Data
Oct. 1, 2010 (IT) ................. FI2010A0206

(51) Int. Cl.
*A61K 9/127* (2006.01)
*A61K 38/17* (2006.01)
*A61K 47/48* (2006.01)

(52) U.S. Cl.
CPC ........... *A61K 9/1271* (2013.01); *A61K 38/1709* (2013.01); *A61K 47/48238* (2013.01); *A61K 47/48815* (2013.01); *A61K 47/48861* (2013.01)

(58) Field of Classification Search
CPC ............... A61K 38/1709; A61K 47/48238; A61K 47/48815; A61K 47/48861; A61K 9/1271
USPC .............. 424/174.1, 450; 514/13.5, 51
See application file for complete search history.

(56) References Cited

U.S. PATENT DOCUMENTS

| 2007/0218116 A1 | 9/2007 | Schwendener | |
| 2009/0087494 A1* | 4/2009 | Kompella et al. | 424/499 |
| 2010/0015068 A1* | 1/2010 | Karp et al. | 424/57 |
| 2013/0184835 A1* | 7/2013 | Ferrari et al. | 623/23.61 |

FOREIGN PATENT DOCUMENTS

| WO | 01/74337 A1 | 10/2001 |
| WO | 2004/058275 A2 | 7/2004 |
| WO | 2007/028020 A2 | 3/2007 |
| WO | 2008/005509 A2 | 1/2008 |
| WO | 2008/008917 A2 | 1/2008 |
| WO | 2009/105584 A1 | 8/2009 |
| WO | 2009/121935 A2 | 10/2009 |

OTHER PUBLICATIONS

Boudou-Rouquette, P. et al., "Antitumoral effect of the bisphosphonate zoledronic acid against visceral metastases in an adrenocortical cancer patient", Annals of Oncology, 2009, vol. 20, pp. 1747-1752.
Caraglia, M. et al., "Emerging anti-cancer molecular mechanisms of aminobisphonates", Endocrine-Related Cancer, 2006, vol. 13, pp. 7-26.
Gnant, M. et al., "Endocring Therapy plus Zoledronic Acid in Premenopausal Breast Cancer", The New England Journal of Medicine, 2009, vol. 360, No. 7, pp. 679-691.
Jagdev, SP et al., "The bisphosphonate zoledronic acid, induces apoptosis of breast cancer cells: evidence for synergy with paclitaxel", British Journal of Cancer, 2001, vol. 84, No. 8, pp. 1126-1134.
Kijima, T. et al., "Lung and bone metastases from renal cell carcinoma responsive to bisphosphonates: A case report", International Journal of Urology, 2008, vol. 15, pp. 546-547.
Lee, M.V. et al., "Bisphosphonate Treatment Inhibits the Growth of Prostate Cancer Cells", Cancer Research, 2001, vol. 61, pp. 2602-2608.
Mackie, PS et al., "Bisphosphonates regulate cell growth and gene expression in the UMR 106-01 clonal rat osteosarcoma cell line", British Journal of Cancer, 2001, vol. 84, No. 7, pp. 951-958.
Okamotoo, K. et al., "Zoledronic acid-induced regression of multiple metastases at nonskeletal sites", Annals of Oncology, 2009, vol. 20, No. 4, pp. 796-797.
Riebeling, C. et al., "The bisphosphonate pamidronate induces apoptosis in human melanoma cells in vitro", British Journal of Cancer, 2002, vol. 87, pp. 366-371.
Senaratne, SG et al., "Bisphosphonates induce apoptosis in human breast cancer cell lines", British Journal of Cancer, 2000, vol. 82, No. 8, pp. 1459-1468.
Shipman, C.M. et al., "The Bisphosphonate Incadronate (YM175) Causes Apoptosis of Human Myeloma Cells in Vitro by Inhibiting the Mevalonate Pathway", Cancer Research, 1998, vol. 58, pp. 5294-5297.
Sonnemann, J. et al., "The biosphonate pamidronate is a potent inhibitor of human osteosarcoma cell growth in vitro", Anti-Cancer Drugs, 2001, vol. 12, pp. 459-465.

* cited by examiner

*Primary Examiner* — Janet Epps-Smith
(74) *Attorney, Agent, or Firm* — Fish & Tsang, LLP

(57) ABSTRACT

The present invention describe nanocomplexes also called auto-assembling nanoparticles comprising biphosphonates, lipid nanovectors and inorganic nanovectors.
In particular the invention describes zoledronic acid complexed with calcium phosphate base nanoparticles; said particles in their turn mixed with lipidic particles e.g. liposomes. Said nanocomplexes are useful, and showed to be efficient in vivo, as pharmaceutical formulations of biphosphonates for the treatment or prevention of tumor growth and/or metastasis. Tumors can be solids and/or haematological such as prostate, lung, head/neck, colon, liver, breast, pancreas, kidneys, bladder, male and female urogenital tract, bones, multiple myeloma, primitive and secondary tumors of the central nervous system and lymphomas.

15 Claims, 2 Drawing Sheets

SELF-ASSEMBLING NANOPARTICLES FOR THE RELEASE OF BISPHOSPHONATES IN THE TREATMENT OF HUMAN CANCERS

PRIORITY

This application is a U.S. National Phase of PCT/EP11/67119 filed on Sep. 30, 2011, which claims priority to Italian Patent Application No. FI2010A000206 filed on Oct. 1, 2010, both of which are incorporated herein by reference in their entirety.

FIELD OF THE INVENTION

The present invention refers to the field of pharmaceutical formulations containing bisphosphonates for the treatment and prevention of human cancers.

STATE OF THE ART

Bisphosphonate (BPs) are the most potent inhibitor of bone resorption and represent the treatment of choice for different diseases, such as osteoporosis, Paget's disease and bone metastases. In oncology, their role in metastatic bone disease is well established, but there is increasing interest in their potential role in preventing and treating cancer-induced bone loss and their possible anti-tumour effects. Increasing evidence is accumulating that BPs are able to directly affect tumour cells, in addition to their direct effects upon osteoclasts. The potency of the antitumour effect in vitro generally mirrors the potency of the anti-resorptive ability with amino-BPs (NBPs), in particular, zoledronic acid (ZOL) being the most potent in both respects. BPs induce apoptosis of tumour cells and inhibit tumour cell growth, in vitro, of a variety of tumour cell types, including breast (Senaratne et al. 2000, Jagdev et al. 2001a), prostate (Lee et al. 2001), melanoma (Riebeling et al. 2002), osteosarcoma (Mackie et al. 2001, Sonnemann et al. 2001) and myeloma (Shipman et al. 1998) tumour cells.

As known, ZOL belongs to the class of NBPs that are used for the treatment of the complications derived from bone metastases so called skeletal related events (pain, spontaneous fractures, bone radiotherapy requirement etc.) and for the prevention of the cancer treatment induced osteopenia (hormone therapy in the treatment of prostate and breast cancer). However, up-to-date ZOL has not still been used as a drug with direct anti-cancer activity and its ability to act directly against bone metastases has never been demonstrated also for the limits of radiologic detection and measurement of cancer in the bone. Moreover, no survival advantage was reported in the patients treated with NBP if compared with patients not treated with NBP, with the exception of the study by M. Gnant et al (N Engl J. Med. 2009) that demonstrates a survival advantage in the adjuvant setting of hormone-dependent breast cancer treated with ZOL.

On the other hand, direct effects on tumour mass induced by ZOL have been never reported with the exception of sporadic case reports (Kijima et al. Int J. Urol. 2008; Okamoto et al. Ann Oncol. 2009; Boudou-Rouquette et al. Ann Oncol. 2009).

One of the most important limits of NBPs, which makes the direct anti-cancer activity difficult to demonstrate in vivo, is their pharmacokinetic profile. In fact, there is rapid elimination of ZOL from plasma resulting from renal excretion and rapid uptake and accumulation within bone. An intravenous administration of ZOL at the dose of 4 mg over 15 min results in a sharp increase in its concentration, with estimated distribution and elimination plasma half-lives of 15 min (t1/2) and 105 min (t1/2β) respectively. The maximum plasma concentration (Cmax) of ZOL is about 1 µM; that is 10- to 100-fold less than that required in vitro studies to induce apoptosis and growth inhibition in tumor cell lines. Moreover, approximately 55% of the initially administered dose of the drug is retained in the skeleton, from which it is slowly released back into circulation (Caraglia M. et al. Endocr Relat Cancer. 2006).

In the light of these considerations, there is a need to develop new ZOL formulations with a lower affinity for bone and a longer half-life in the circulation that would result in increased probability to affect peripheral tumours. At the state of the art it is known that employing nanotechnologies, and in particular stealth liposomes (that is those comprising hydrophilic polymers, e.g. polyethylenglycol or PEG, in their compositions), allows the use of ZOL in several tumors (US2007/0218116; IT FI2009A000190 in the name of the same Applicants). In particular, the employ of ZOL containing liposomes allows a considerable tumor growth reduction in different cancer animal models. In the same animal model the tumors resulted to be resistant to ZOL.

However, the formulation strategy developed so far present some inconvenient such as a reduced liposomes physical stability which requires the liposomes to be lyophilised, a low encapsulation efficiency (about 5% corresponding to 100 µg ZOL/mg of lipids) and a certain drug loss following rehydratation after lyophilization.

WO2008/005509) in which BPs are used as hydroxyapatite binding agents. The invention describes particles in which BP is used to bind biological surface, such as tooth or bone. Moreover, the patent application WO2008/005509 describes PLGA-PEG nanoparticles chemically conjugated at the carboxyl terminal to a biphosphonate which were added in trace amount to a solution of CaCO3 (average size 800 nm) resulting in an aggregation of the CaCO3 particles. Such a composition is suitable for delivering particles to a tooth or bone. Thus, this composition can be used to modify biological surface of tooth or bone, while is not suitable to avoid BP accumulation into the bone and cannot be used to target tumors.

It is therefore evident the need of providing pharmaceutical formulations containing NBPs which overcome the above said problems and are efficient for the treatment of tumors.

SUMMARY OF THE INVENTION

The object of the present invention are nanocomplexes, also called nanoparticles (NP), containing bisphosphonates complexed with inorganic and lipid nanovectors; wherein the biphosphonate is first complexed to inorganic nanovectors and the resulting particles are then complexed to lipid nanovectors and wherein the inorganic nanovectors consist of nanoparticles of a Ca-, Mg-, Sr- or Zn-inorganic salt. The aforementioned nanocomplexes can be also named self-assembling nanoparticles. The aforementioned nanocomplexes are useful as pharmaceutical formulation for the treatment or the prevention of tumor growth and/or metastasis. The tumors can be solid or haematological tumors, such as prostate cancer, lung cancer, head/neck cancer, colon cancer, liver cancer, breast cancer, pancreas cancer, kidney cancer, bladder cancer, male and female urogenital tract cancer, bone cancer, multiple myeloma, melanoma, lymphoma, primitive and secondary tumors.

In particular, the invention related to a bisphosphonate, for example the zoledronic acid (ZOL), complexed with nanoparticles based on calcium and phosphate salts; such particles are mixed with other particles, for example liposomes. The nanocomplexes, object of this invention, have advantages such as the possibility to be easily prepared immediately before use, a high drug loading, a high reproducibility of the results. Nanocomplexes, according with this invention, are nanoparticulate entities, for which, surprisingly, imagines were acquired by cold field electron gun scanning electron microscopy (cFEG-SEM) (FIG. 1). These nanocomplexes have a mean diameter ranging form 10 to 500 nm. Moreover, such system has showed an antitumor effect higher than that observed with ZOL-containing liposomes previously developed (Marra et al. Biotechnology Advances 2011).

DETAILED DESCRIPTION OF THE INVENTION

Figure 1:
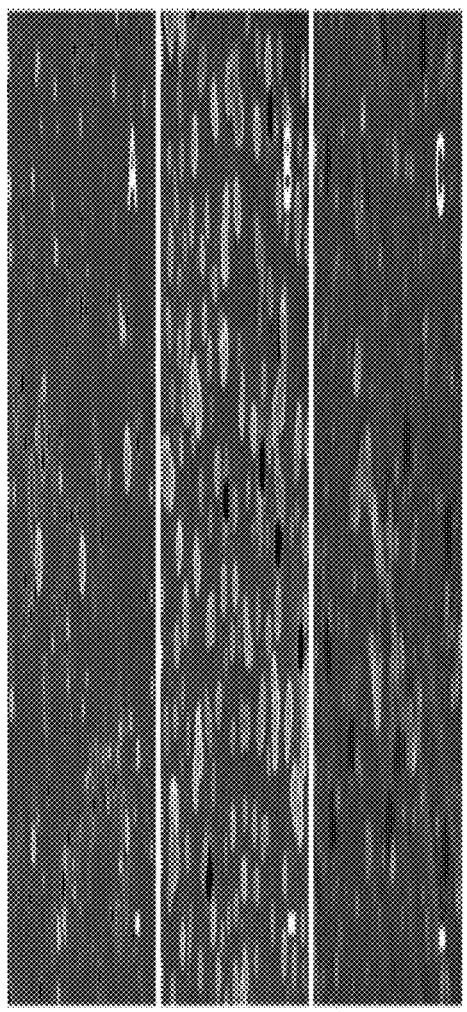
FIG. 1—It shows images of cFEG-SEM, acquired with a magnification of 40,000×, of the surfaces of some embodiment nanocomplexes or NPs, according with the invention.

It has been surprisingly found, and it is object of the present invention, that bisphosphonates, in pharmaceutical formulation based on the combination of lipid and inorganic nanovectors can be successfully used for the treatment of different solid and haematological tumors, such as prostate cancer, lung cancer, head/neck cancer, colon cancer, liver cancer, breast cancer, pancreas cancer, kidney cancer, bladder cancer, male and female urogenital tract cancer, bone cancer, multiple myeloma, melanoma, lymphomas.

In a preferred embodiment ligands can be added on the NP surface in order to target specific cells. Ligands can be selected among those having specificity for receptors that are overexpressed on specific cells, for example cancerous cells, but are normally or minimally expressed on normal, healthy cells. These molecules should have high affinity to their cognate receptors, plus can have innate abilities to induce receptor-mediated endocytosis. The targeting layer poses as the outmost exterior of the NP, where targeting ligands are generally presented on top of the stealth layer. Structures such as antibodies, antibody fragments, proteins, small molecules, aptamers and peptides have all demonstrated abilities to induce NP-targeting to cancer cells (M. Wang and M. Thanou, Pharmacological Research 2010; Huynh, et al. Nanomedicine 2010.). As representative embodiment, NP with human-transferrin on their surface were prepared and characterized (see experimental section).

The Formulation can be administered to the patient by parenteral administration, for example by intravenous, intraperitoneal, intratumoral, intrarterial injection, depending on the type of tumor to treat. Other routes of administration, such as oral or transdermal, cannot be excluded.

The formulation can be used for different BPs, such as clodronate, alendronate, etidronate, pamidronate, tiludronate, ibandronato, neridronato, zoledronate, minodronate and risedronate, and their biological derivates or prodrugs. The selected BP is preferably the zoledronic acid.

The amount of BP loaded into the nanoparticles is preferably comprised between a. µg e 100 mg di BP/ml of suspension, more preferably between 50 µg and 0.250 mg BP/ml of suspension.

According with the invention, the nanovectors are structures with a size ranging between ten and hundreds of nanometers able, when associated to a drug, to change its pharmacokinetic profile.

According with the invention, the nanovectors are nanoparticles, nanocapsules or nanospheres, liposomes or other nanovectors such as niosomes, micelles.

In the present invention, self-assembling nanoparticles are preferred.

According with our invention, the nanovectors have to be preferably prepared by mixing of solutions and/or dispersions. In particular, the formulation, consists in self-assembling nanovectors prepared before use.

According to the invention, the nanovectors can be prepared by mixing two or more aqueous or organic solutions or suspensions.

According the invention, the nanovectors can be lipid or polymeric nanoparticles, for example liposomes or other nanovectors such as niosomes and micelles.

These nanovectors are preferably self-assembling nanoparticles, preferably stealth nanoparticles (NPs bearing an hydrophilic polymer, i.e. polyethylene glycol or PEG, on their surface).

According with the invention, the self-assembling nanoparticles are preferably formed starting from inorganic nanoparticles and lipid nanovectors.

In particular, according with the invention, the inorganic nanovectors are nanoparticles based on inorganic salts. For example and preferably, it is possible to use nanoparticles based on inorganic salts containing Ca, Mg, Sr, Zn, and mixtures thereof. Preferably, these inorganic nanovectors are based on Ca and P and, in particular, on nanoprecipitated calcium hydrogen phosphate.

The lipid nanovectors are preferably liposomes, preferably composed on phosphoglycerides and sfingolipids, together with their products of hydrolysis, sterols, cationic lipids, anionic lipids, neutral lipids, lipids conjugated with synthetic or natural polymers or lipids bound to fluorescent probes, or lipids bound to proteins or peptides, or lipids conjugated with molecules able to specifically interact with receptor of the cell membrane. In particular, these liposomes are based on mix of 1,2-dioleoyl-3-trimethylammonium-propane (chloride salt) (DOTAP), cholesterol, 1,2-distearoyl-sn-glycero-3-phosphoethanolamine-N-[methoxy(polyethylene glycol)-2000] (DSPE-PEG 2000), preferably in amount ranging between 0-100%, 0-80% and 100-0% (p/p), respectively.

In a preferred embodiment, DSPE-PEG 2000 is premixed with the other components of the liposomal mix.

For an aspect, the invention concerns to a method for the preparation of the complexes, comprising the following steps:
 a. mixing of a suspension containing inorganic nanovectors with a solution containing the bisphosphonate, to obtain a suspension of the bisphosphonate complexed to the nanovectors;
 b. mixing of a suspension of the lipid nanovectors with the suspension obtained from the step a.

For preparing NPs bearing a ligand for receptors overexpressed by cancer cells the ligand can be added, incubating the NP obtained according to the process as above described, in a solution containing the ligand; or, in alternative, it can be included in the NP first incubating the lipid nanovectors in a solution containing the ligand and then mixing the obtained ligand-nanovectors complexes or conjugated with the suspension obtained from the step a.

For an aspect the invention concerns a kit to prepare the aforementioned pharmaceutical formulations; such kit contains:
- at least a container containing a bisphosphonate, in solution or at the solid state;
- at least a container containing a suspension of inorganic nanovectors;
- at least a container containing a suspension containing lipid nanovectors.

Preferably the kit according to the invention can include at least a container containing a ligand, or a solution thereof, for receptors overespressed in cancer cells. Alternatively, the ligand can be already present into the container containing a suspension containing lipid nanovectors.

The present invention can be better understood from the following examples.

EXAMPLE 1

Preparation of Stealth Self Assembly Nanoparticles Containing ZOL

Ingredients: calcium chloridre 18 mM, hydrogen phosphate dibasic 10.8 mM, 10 or 50 mg of zoledronic acid. 1,2-dioleoyl-3-trimethylammonium-propane chloride (DOTAP) and 1,2-diacyl-sn-glycero-3-phosphoethanolamine-N-[methoxy(polyethylene glycol)-2000] (DSPE-PEG2000) cholesterol (chol).

Step 1: Preparation of Calcium Phosphate Nanoparticles and their Complexes with ZOL An aqueous solution of calcium chloride (18 mM) was added, dropwise and under magnetic stirring, to an aqueous solution on dibasic hydrogen phosphate (10.8 mM). The pH of both solutions was adjusted beforehand to 9.5 with NaOH. CaP NPs were obtained by filtration of the suspension through a 0.22 μm filter. CaP NPs were stored at 4° C. before use. CaP/ZOL-NPs complexes (CaPZ NPs) were prepared by mixing a CaP NPs dispersion with an aqueous solution of ZOL at different ZOL concentrations (10 mg/ml of ZOL in water or 50 mg/ml of ZOL in phosphate buffer at pH 9.5), at a volume ratio of 50:1.

Step 2: Preparation of Liposomes

Liposomes consisting of DOTAP/chol (1:1 weight ratio) or DOTAP/chol/DSPE-PEG 2000 (1:1:0.5 or 1:1:1 weight ratio) were prepared by hydration of a thin lipid film followed by extrusion. Briefly, the lipid mixture were dissolved in 1 ml of a mixture chloroform/methanol (2:1 v/v), the resulting solution was added to a 50 ml round-bottom flask, and the solvent was removed under reduced pressure by a rotary evaporator under nitrogen atmosphere. Then, the lipid film was hydrated with 1 ml of sterile water and the resulting suspension was gently mixed in the presence of glass beads, after that the flask was left at room temperature for still 2 h. The liposome suspension was then extruded using a thermobarrel extruder system passing repeatedly the suspension under nitrogen through polycarbonate membranes with decreasing pore sizes (0.4-0.1 μm). After preparation, liposomes were stored at 4° C. Each formulation was prepared in triplicate.

Step 3: Preparation of Self Assembly Nanoparticles Containing ZOL

CaP ZOL NP obtained according to Step 1 were mixed with cationic liposomes obtained according to Step 2. Briefly, 500 μl of CaPZ NPs were mixed with 500 μl of DOTAP/chol liposomes, at a final ZOL concentration 0.25 or 0.05 mg/ml suspension. One milliliter of a LCaPZ NPs suspension was then mixed with 50 μl micellar dispersion of DSPE-PEG2000 (47 mg/ml) and then incubated at 50-60° C. for 10 min. The resulting suspension (post-PLCaPZ NPs) was then allowed to cool to room temperature before use.

EXAMPLE 2

Preparation of Stealth Self Assembly Nanoparticles Containing ZOL

Ingredients: calcium chloridre 18 mM, hydrogen phosphate dibasic 10.8 mM, 10 or 50 mg of zoledronic acid. 1,2-dioleoyl-3-trimethylammonium-propane chloride (DOTAP) and 1,2-diacyl-sn-glycero-3-phosphoethanolamine-N-[methoxy(polyethylene glycol)-2000] (DSPE-PEG2000) cholesterol (chol).

Step 1 and Step 2 was similar to that described in Example 1.

Step 3:

Equal volumes of suspensions containing DOTAP/chol/DSPEG2000 liposomes and CaPZ NPs, respectively, were mixed in a glass tube and the resulting dispersion was allowed to stand at room temperature for 10 min (pre-PLCaPZ NPs).

Nanoparticles Characterization

The mean diameter of cationic liposomes and PLCaPZ NPs, were determined at 20° C. by photon correlation spectroscopy (PCS). Each sample was diluted in deionizer/filtered water and analyzed with detector at 90° angle. As measure of the particle size distribution, polydispersity index (P.I) was used. For each batch, mean diameter and size distribution were the mean of three measures. For each formulation, the mean diameter and P.I. were calculated as the mean of three different batches.

The zeta-potential (ζ) of the NPs surface was measured in water by means of a Zetasizer Nano Z. Data of ζ were collected as the average of 20 measurements.

Morphological analysis of LCaPZ, post- and pre-PLCaPZ NPs were investigated by cold field emission gun-scanning electron microscopy (cFEG-SEM), as reported by De Rosa et al. (De Rosa et al. International Journal of Pharmaceutics 2008). For cFEG-SEM analysis, samples were prefixed in a mix of 4% formaldehyde and 1% glutaraldehyde in distilled water for 1 h. Then, samples were rinsed in distilled water by ultracentrifugation (80,000 rpm) and post-fixed by adding 1% OsO4 for 1 h. After a further washing with distilled water, pellets were filtered on a polycarbonate filter (0.1 μm) in a Swinnex filtration apparatus (Millipore, USA). A second filter was placed over the first to form a sandwich in which liposomal pellets were trapped. Samples were then dehydrated in a graded alcohol series (10, 30 and 50% for 10 min, 70 and 80% for 30 min, 95% for 1 h and 100% overnight at 4° C.) and critically point dried. At the end of the treatment, the Swinnex was opened and both filters were placed on a stub cleaned with acetone to remove any grease. Double adhesive carbon disks (EMS, USA) were stuck onto the stub, and the filters containing the samples were placed over it. Finally, the stubs were sputter coated with a nanometric layer of gold. Observations were carried out by a cold cathode Field Emission Gun Scanning Electron Microscope (FEG Jeol 6700F, Jeol Ltd., Japan). The pictures of the NPs surface at higher magnifications were taken at 2-5 kV (see FIG. 1).

ZOL analysis was carried out by reverse phase high performance liquid chromatography (RP-HPLC). The HPLC system consisted of an isocratic pump equipped with a 7725i injection valve, SPV-10A UV-Vis detector set at the wavelength of 220 nm. The system was controlled by a SCL-10A VP System Controller connected with a computer. Chromatograms were acquired and analysed by a Class VP Client/Server 7.2.1 program. The quantitative analysis of ZOL was performed on a Gemini 5 μm C18 column (250×4.60 mm, 110 Å Phenomenex, Klwid, USA) equipped with a security guard. The mobile phase was a mixture 20:80 (v/v) of acetonitrile and an aqueous solution (8 mM di-potassium hydrogen orthophosphate, 2 mM di-sodium hydrogen orthophosphate and 7 mM tetra-n-butyl ammonium hydrogen sulphate, adjusted at pH of 7.0 with sodium hydroxide). ZOL determination was performed in isocratic condition, at a flow rate of 1 ml/min at room temperature.

For CaPZ, post and pre-PLCaPZ NPs the amount of un-complexed ZOL was determined as follows: 1 ml of NPs dispersion was ultracentifugated (Optima Max E, Beckman Coulter, USA) at 80.000 rpm at 4° C. for 40 min. Supernatants were carefully removed and ZOL concentration was determined by RP-HPLC. The results have been expressed as complexation efficiency, calculated as the ratio between the amount of ZOL present in the supernatants and the amount of ZOL theoretical loaded.

Cell Culture and Proliferation Assay.

Human melanoma cells (M14) and doxorubicin resistant cells (M14+) were provided by Prof. G. Arancia form the National Institute of Health of Rome. All the other cell lines were provided by ATCC and were grown in medium as suggested by ATCC in a humidified atmosphere of 95% air/5% $CO_2$ at 37° C. Proliferation of human cancer cell lines was performed in the presence of increasing concentrations of different drugs by MTT assay as previously described by Caraglia et al. (Oncogene 2004).

In Vivo Experiment

CD-1 nude (nu/nu) mice, 6-8 weeks old were purchased from Charles River Laboratories (Milano, Italy).

Mice have been acclimated for one week before to be injected with tumor cells. Mice were injected intramuscularly with tumor cells at 3×106 cells/mouse in 200 μl of PBS. Six days after, a tumor mass of about 0.3 $cm^3$ in diameter was evident, mice were randomized in four groups. Six mice/group were treated with ZOL free or NP containing ZOL for 3 consecutive weeks. Tumor mass was calculated three times a week from caliper measurements by using the formula π/6 AB, where A is the major diameter and B is the minor diameter, corresponding to tumor mass (Sommer K. et al. International Journal of Oncology 2001). Toxicity was evaluating by measuring the body weight two times a week. Student's t test was used for statistical comparison of differences.

PC3M-luc2 is a luciferase expressing cell line which was stably transfected with the luc2 firefly luciferase gene (Caliper Life Sciences, Hopkinton, Mass., USA). Human xenografts were imaged using the IVIS imaging system 200 series (Caliper Life Sciences). Briefly, mice were anesthetized with a combination of tiletamine-zolazepam (Telazol, Virbac, Carros, France) and xylazine (xylazine/Rompun BAYER) given intramuscularly at 2 mg/kg. Then mice were injected intraperitoneally with 150 mg/kg D-luciferin (Caliper Life Sciences), and imaged in the supine position 10-15 min after luciferin injection. Data were acquired and analyzed using the living image software version 3.0 (Caliper Life Sciences).

Evaluation of Apoptosis by TUNEL Technique

For TUNEL assay, after washing in PBS supplemented in 0.1% BSA, cells were treated with an in situ detection kit, according to the manufacturers instructions (Boehringer Mannheim Biochemicals). Nuclei with fragmented DNA were visualized by a fluorescence microscope.

Characteristic of the Formulations Object of the Invention

The characteristics of the formulation containing ZOL are reported in table 1. We obtained pre-PLCaPZ NP with a mean diameter of about 150 nm with PI<0.2. The actual loading of ZOL in pre-PLCaPZ NP was of about 0.175 mg/ml of dispersion, corresponding of a complexation efficiency of about 70%. On the contrary, post-PLCaPZ NP were characterized by a high mean diameter, around 300 nm, and an heterogeneous size distribution (IP=0.3). In addition, the amount of ZOL loaded in post PLCaPZ NP was 5 times lower than that found in pre PLCaPZ NP, since an increase in concentration of ZOL from 0.05 to 0.25 results in aggregates formation. We also investigated morphological characteristics of LCaPZ NPs, pre and post-PLCaPZ NPs by cFEG-SEM analysis (FIG. 1). In the case of LCaPZ NPs, regularly shaped NPs with a smooth surface were observed (FIG. 1A). On the other hand, the analysis of the formulation containing pre-PLCaPZ NPs showed irregularly shaped particles with homogeneous size distribution and a rather rough surface (FIG. 1B). On the contrary, the formulation containing post-PLCaPZ NP was characterized by an heterogeneous particles dispersion (1C).

TABLE 1

Diameter, P.I., zeta potential (ζ) and complexation efficiency of post and pre-PLCaPZ NPs.

| Formulation | Mean diameter (nm) ± SD | P.I. ± SD | ζ (mV) ± SD | ZOL theorical loading (mg/ml) | Complexation efficiency (% ± SD) |
|---|---|---|---|---|---|
| Post-PLCaPZ NPs | 309.1 ± 163.0 | 0.363 ± 0.2 | 10.7 ± 5.5 | 0.05 | 100.0 ± 0.0 |
| Pre-PLCaPZ NPs | 147.5 ± 7.1 | 0.152 ± 0.06 | 17.5 ± 5.6 | 0.250 | 66.0 ± 1.0 |

FIG. 1. Images from cFEG SEM analysis. (A) LCaPZ NPs; (B) Pre-PLCaPZ NPs; (C) Post-PLCaPZ NPs. Scale bar 100 nm.

In Vitro Anti-Tumour Activity of ZOL, Alone or Encapsulated in NPS in Different Cancer Cell Lines.

It was studied the effect of increasing concentrations of ZOL encapsulated in pre- and post-PLCaP NPs on growth inhibition of different human cancer cell lines, by MTT assay. In Table 2, the IC50 (50% inhibitory concentration) values of ZOL, free or encapsulated in pre- or post-PLCaP NPs, in the different cell lines analysed after 72 h, are reported. In all cases, when considering blank NPs, the cytotoxicity of post-PLCaP NPs was significantly higher than that observed for pre-PLCaP NPs. Moreover, when using ZOL-encapsulating NPs, we found a potentiation factor (PF)>1.0 in all tested cell lines, if compared with the free ZOL. The two tested formulations showed different efficiency to deliver ZOL to the cells, and this effect was strictly dependent on the cell line, with the highest cell growth inhibition obtained on breast cancer cells. In particular, on MCF7, pre-PLCaPZ NPs caused an about 12-fold potentiation of ZOL-induced cytotoxicity, while a lower effect (about 8-fold) was found with post-PLCaP NPs.

TABLE 2

Growth inhibition and potentiation factors on tumor cell lines of different histological derivation.

| Cell lines | free ZOL | Post-PLCaPZ NPs | Blank Post-PLCaP NPs | P.F. | Pre-PLCaPZ NPs | Blank Pre PLCaP NPs | P.F. |
|---|---|---|---|---|---|---|---|
| Prostate | | | | | | | |
| PC3 | 12.5 | 2.2 | 23 | 5.7 | 3.6 | 57.4 | 3.5 |
| DU145 | 25 | 7.4 | 42 | 3.4 | 11.6 | 120 | 2.2 |
| Breast | | | | | | | |
| MCF7 | 120 | 14.7 | 33.3 | 8.1 | 10.1 | 120 | 11.8 |
| MDA-MB468 | 28.4 | 13 | 65 | 2.2 | 11.3 | 120 | 2.5 |
| CG5 | 74 | 7.5 | 30 | 9.9 | 16 | 120 | 4.6 |
| Head/neck | | | | | | | |
| KB | 22.8 | 5.6 | 19.4 | 4.07 | 11.1 | 120 | 2 |
| Lung | | | | | | | |
| H1355 | 65 | 11 | 35 | 5.9 | 9.5 | 86 | 6.8 |
| Pancreas | | | | | | | |
| Panc | 32 | 12.7 | 44.5 | 1.4 | 18.5 | 84.8 | 1.6 |
| BX-PC3 | 12.3 | 11.8 | 44.6 | 1.04 | 9 | 22 | 1.4 |
| MIA PaCa | 55 | 16.8 | 46 | 3.3 | 42 | 120 | 1.3 |
| Multiple Myeloma | | | | | | | |
| RPMI | 120 | 15.5 | 66 | 7.7 | 90 | 120 | 1.3 |
| DOX | 41.9 | 35 | 42 | 1.2 | 13.8 | 120 | 3 |
| KMS | 30 | 2.3 | 11.8 | 13 | 8 | 44.6 | 3.8 |
| OPM2 | 83 | 35 | 69.7 | 2.4 | 33 | 95 | 2.5 |

In Vivo Evaluation of Antitumoral Activity of Formulations Containing ZOL on Prostate Cancer PC-3 cells were injected into the left hind leg muscles of nude mice and six days after (when a tumor mass was evident) treatment started by intravenously injection of 20 µg of ZOL free or complexed with pre PLCaPZ NP, a formulation selected for the best technological characteristics. As control, a group of mice was treated with NP not containing ZOL, to evaluate the potential antitumoral effects. Mice were treated three times a week for three consecutive weeks. Antitumor efficacy of treatments was assessed by the following endpoints: a) percent tumor weight inhibition (TWI %), calculated as [1-(mean tumor weight of treated mice/mean tumor weight of controls)]×100; b) tumor growth delay, evaluated as T–C, where T and C are the median times for treated (T) and untreated tumors (C), respectively, to achieve equivalent size. The results reported in the table 3 show a growth inhibition of 17% in mice treated with ZOL free thus suggesting that PC-3 tumors are resistant to ZOL. On the contrary, ZOL complexed with pre PLCaPZ NP produce 44% inhibition of tumor growth. So, the release of ZOL from NP is able to sensitize PC-3 cells to ZOL antitumoral effects. A comparison between stealth liposomes containing ZOL and pre PLCaPZ NP highlighted the major efficacy of the pre PLCaPZ NP formulation. In fact, this formulation produced a 10% increased antitumor efficacy compared to stealth liposomes.

TABLE 3

Antitumor activity of ZOL, alone or encapsulated into the self-assembling NPs.

| Treatment* | TWI (%) § | T-C (days) & |
|---|---|---|
| ZOL 20 µg | 17 | 5 |
| Blank stealth liposome | 12 | 3 |
| Stealth liposome containing ZOL 20 µg | 35 | 9 |
| Blank NPs | 18 | 2 |
| ZOL encapsulating NPs | 44 | 11 |

*Days of treatment: 6, 8, 13, 15, 17, 20, 22, 24 after tumor cells injection. Drugs have been injected intravenously three times a week for three consecutive weeks. Treatment started six days after the tumor cells injection.
§ Percent tumor weight inhibition calculated at the nadir of the effect.
& Tumor growth delay, where T and C are the median times for treated (T) and untreated tumors (C), respectively, to achieve equivalent size.

Bioluminescence Imaging Analysis

Figure 2:
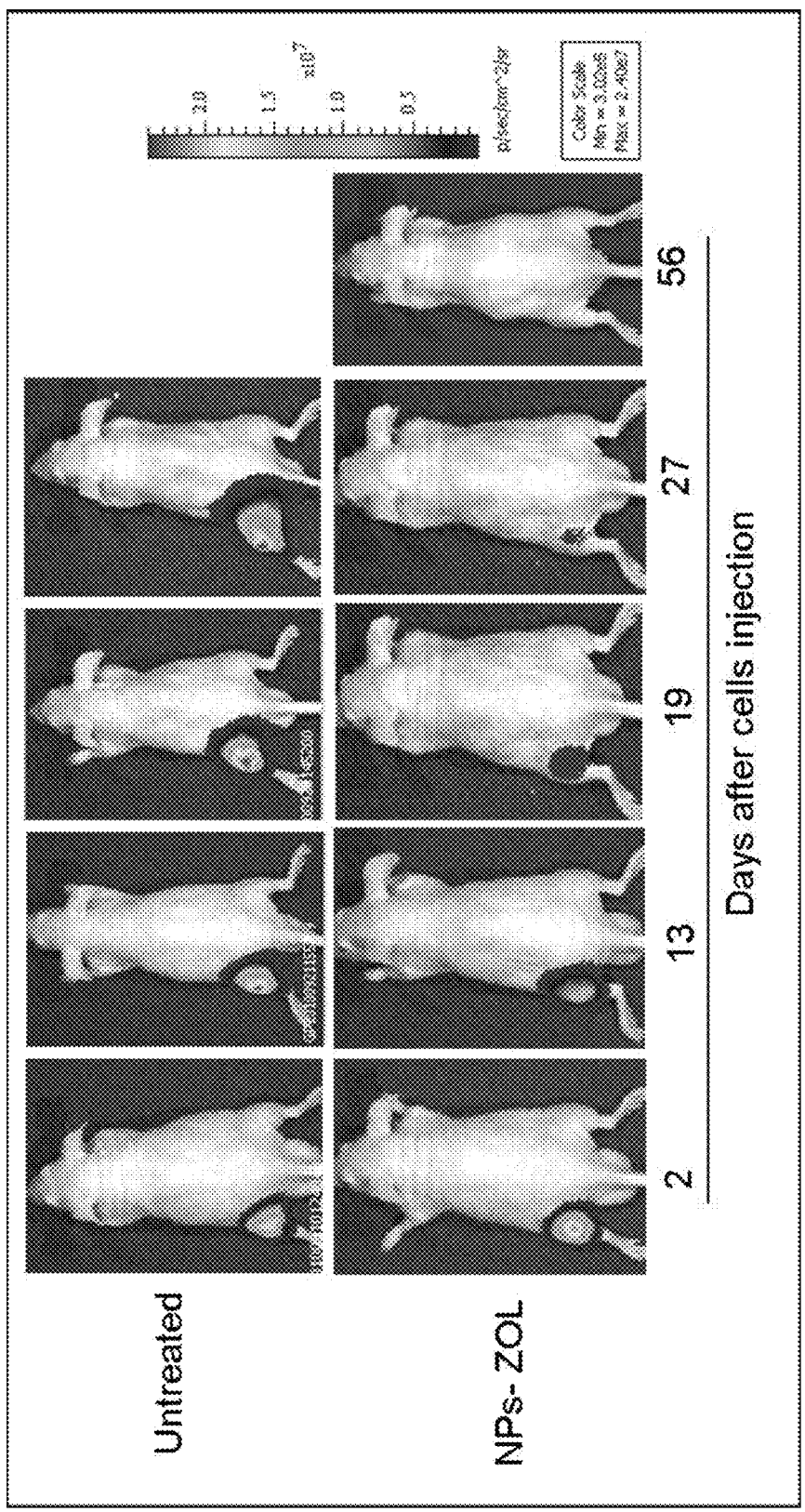
FIG. 2. Example of luminescence associated to injected tumour cells in an untreated mouse (upper panel) and in a mouse treated with nanocomplex according to the invention (PLCaPZ NPs; lower panel) achieving a complete regression of the tumour after 56 days from the initial tumour cell injection.

After 4 months from tumor cell injection, no tumour was evident with both palpability and at the analysis of luminescence with a dedicated apparatus (FIG. 2) in animal treated with PLCaPZ NPs. In this mouse a progressive reduction of the luminescence associated to the tumour cells was observed with a complete regression of the luminescence at 56 days from the tumour cell injection. Blank PLCaPZ NPs did not induce any significant effect on the tumour weight if compared to free ZOL and untreated groups (data not shown). Finally, it is interesting to note that all the treatments were well tolerated by animals since no body weight loss and toxic deaths have been observed.

EXAMPLE 3

Functionalization of Self-Assembling NPs Containing ZOL Bearing Human Transferrin on Their Surface Ingredient: 18 mM of calcium chloridre, 10.8 mM of hydrogen phosphate dibasic, 50 mg of zoledronic acid. 1,2-dioleoyl-3-trimethylammonium-propane chloride (DOTAP) and 1,2-diacyl-sn-glycero-3-phosphoethanolamine-N-[methoxy(polyethylene-glycol)-2000] (DSPE-PEG2000) cholesterol (chol), 0.1 mM of human transferrin (Tf).
Step 1: Preparation of PEGylated Cationic Liposomes Liposomes consisting of DOTAP/chol/DSPE-PEG 2000 (1:1:0.5 weight ratio) were prepared by hydration of a thin lipid film followed by extrusion. Briefly, the lipid mixture were dissolved in 1 ml of a mixture chloroform/methanol (2:1 v/v), the resulting solution was added to a 50 ml round-bottom flask, and the solvent was removed under reduced pressure by a rotary evaporator under nitrogen atmosphere. Then, the lipid film was hydrated with 1 ml of sterile water and the resulting suspension was gently mixed in the presence of glass beads, after that the flask was left at room temperature for still 2 h. The liposome suspension was then extruded using a thermobarrel extruder system passing repeatedly the suspension under nitrogen through polycarbonate membranes with decreasing pore sizes (1.4-0.4 µm). After preparation, liposomes were stored at 4° C. Each formulation was prepared in triplicate.
Step 2: Preparation of Calcium Phosphate Nanoparticles and their Complexes with ZOL An aqueous solution of calcium chloride (18 mM) was added, dropwise and under magnetic stirring, to an aqueous solution on dibasic hydrogen phosphate (10.8 mM). The pH of both solutions was adjusted beforehand to 9.5 with NaOH. CaP NPs were obtained by filtration of the suspension through a 0.22 µm filter. CaP NPs were stored at 4° C. before use. CaP/ZOL-NPs complexes (CaPZ NPs) were prepared by mixing a CaP NPs dispersion with an aqueous solution of (50 mg/ml of ZOL in phosphate buffer at pH 9.5), at a volume ratio of 50:1.

Step 3: Preparation of Self-Assembly NPs Containing ZOL

Equal volumes of suspensions containing DOTAP/chol/DSPEG2000 liposomes, prepared according to Step 1, and CaPZ NPs, prepared according to Step 2, were mixed in a glass tube and the resulting dispersion was allowed to stand at room temperature for 10 min (PLCaPZ NPs).

Step 4: Preparation of Post-Tf-PLCaPZ NPs

PLCaPZ NPs bearing Tf on their surface (post-Tf-PLCaPZ NPs) were prepared by incubation of PLCaPZ NPs dispersion, prepared according to Step 3, with Tf solutions (10 mg/ml in phosphate buffer at pH 7.4) for 15 min, at room temperature, at a volume ratio of 1:0.5.

EXAMPLE 4

Functionalization of Self-Assembly NPs Containing ZOL Bearing Human Transferrin on their Surface Ingredient: 18 mM of calcium chloride, 10.8 mM of hydrogen phosphate dibasic, 50 mg of zoledronic acid. 1,2-dioleoyl-3-trimethylammonium-propane chloride (DOTAP) and 1,2-diacyl-sn-glycero-3-phosphoethanolamine-N-[methoxy(polyethylene-glycol)-2000] (DSPE-PEG2000) cholesterol (chol), 0.1 mM of Tf.

Step 1: Preparation of Transferrin-PEGylated Cationic Liposomes

Tf-PEGylated cationic liposomes were prepared by pre-incubating of PEGylated cationic liposomes, obtained according to Step 1 of the Example 3, with human transferrin (10 mg/ml in phosphate buffer at pH 7.4) at a volume ratio of 1:1. The resulting liposomes were allowed to stand at room temperature for 15 min before the use.

Step 2: Preparation of pre-Tf-PLCaPZ NPs

Tf-PEGylated cationic liposomes, prepared according to Step 1, were mixing with CaPZ NPs, prepared according to Step 2 of the Example 3, at a volume ratio of 1:0.5. The resulting dispersion was incubated at room temperature for 15 min before the use.

NP Characterization

The mean diameter of Tf-PLCaPZ NPs, were determined at 20° C. by photon correlation spectroscopy (PCS) (N5, Beckman Coulter, Miami, USA). Each sample was diluted in deionizer/filtered (0.22 μm pore size, polycarbonate filters, MF-Millipore, Microglass Heim, Italy) water and analyzed with detector at 90° angle. As measure of the particle size distribution, polydispersity index (P.I) was used. For each batch, mean diameter and size distribution were the mean of three measures. For each formulation, the mean diameter and P.I. were calculated as the mean of three different batches. The zeta-potential (ζ) of the NPs surface was measured in water by means of a Zetasizer Nano Z (Malvern, UK). Data of ζ were collected as the average of 20 measurements. ZOL analysis was carried out by reverse phase high performance liquid chromatography (RP-HPLC). For pre and post-Tf-PLCaPZ NPs, the amount of un-complexed ZOL was determined as follows: 1 ml of NPs dispersion was ultracentifugated (Optima Max E, Beckman Coulter, USA) at 80.000 rpm at 4° C. for 40 min. Supernatants were carefully removed and ZOL concentration was determined by RP-HPLC. The results have been expressed as complexation efficiency, calculated as the ratio between the amount of ZOL present in the supernatants and the amount of ZOL theoretical loaded.

Characteristic of Pre and Post-Tf-PLCaPZ NPs

The characteristics of the formulation containing human transferrin are reported in the table. Both pre and post-Tf-PLCaPZ NPs prepared with the different methods, had a mean diameter of about 150 nm with PI<0.2. Compared with unconjugated NPs, Tf-conjugated NPs (pre and post-Tf-PLCaPZ NPs) showed a significant decrease of the net positive charge of the NPs was observed, confirming the presence of Tf on NP surface.

| Formulations | Mean diameter (nm) ± SD | I.P. ± SD | ζ ± SD |
|---|---|---|---|
| post-Tf-PLCaPZ NPs | 144.4 ± 10.3 | 0.142 ± 0.07 | +9.9 ± 1.5 |
| pre-Tf-PLCaPZ NPs | 147.7 ± 15.0 | 0.169 ± 0.05 | +11.3 ± 1.1 |

The invention claimed is:

1. A nanocomplex, which is a self-assembling nanoparticle, comprising a core portion comprising bisphosphonate complexed with an inorganic nanovectors and an outer portion comprising a lipid and a hydrophilic polymer, wherein the outer portion envelopes the core portion to form the nanocomplex and wherein the nanocomplex is stabilized by non-covalent interactions between the core portion and the outer portion and has a mean diameter between 10 nm and 500 nm; wherein the nanocomplex is assembled by first complexing biphosphonate with the inorganic nanovectors to form the core portion and then subsequently contacting the formed core portion with a lipid nanovector comprising the lipid and the hydrophilic polymer, wherein the inorganic nanovectors comprises nanoparticles of a Ca, Mg, Sr or Zn inorganic salt.

2. The nanocomplex according to claim 1, wherein the outer portion further comprises a ligand for receptors overexpressed by cancer cells.

3. The nanocomplex according to claim 2, wherein the ligand can be selected among antibodies, antibody fragments, proteins, peptides, aptamer and small molecules.

4. The nanocomplex according to claim 3 wherein the ligand is human transferrin.

5. The nanocomplex according to claim 1, wherein said inorganic salt contains Ca and P.

6. The nanocomplex according to claim 1, wherein the lipid nanovector is contacted with the core portion as a liposome.

7. The nanocomplex according to claim 6, wherein said liposome consists of a lipid mixture comprising one or more of the group consisting of phosphodiglycerids and sphingolipids together with their hydrolysis products, sterols, cationic lipids, anionic lipids, neutral lipids, lipids conjugated with synthetic or naturally occurring polymers, lipids linked to fluorescent probes, lipids linked to proteins or peptides, lipids conjugated with molecules capable of specifically interacting with receptors present on a cell membrane.

8. The nanocomplex according to claim 1, wherein said bisphosphonate is selected from clodronate, alendronate, etidronate, pamidronate, tiludronate, ibandronate, neridronate, zoledronate, minodronate and risedronate, and biologically active derivatives or prodrugs thereof.

9. A pharmaceutical formulation comprising a nanocomplex according to claim 1.

10. A method of treating solid or hematological tumors such as prostate, lung, head/neck, colon, liver, breast, pancreas, kidneys, bladder, male and female urogenital tract, multiple myeloma, primitive and secondary tumours of the central nervous system and lymphomas, said method comprising administering to a patient in need thereof a nanocomplex according to claim 1.

11. A process for preparing a nanocomplex according to claim 1, comprising the following steps:
  a. mixing a suspension containing the inorganic nanovectors with a solution containing the bisphosphonate, to obtain a suspension containing bisphosphonate complexed to inorganic nanovectors, and then
  b. mixing a suspension of stealth lipid nanovectors with the suspension obtained from step (a) to generate a nanocomplex according to claim 1.

12. The process according to claim 11 wherein the stealth lipid nanovectors comprise a ligand for receptors overexpressed by cancer cells, said process comprising:
  after step (b) incubating the obtained nanocomplexes with a solution of the ligand;
  or alternatively, before step (b), incubating the stealth lipid nanovectors in a solution containing the ligand and then performing the step (b) mixing the obtained ligand-nanovectors complexes with the suspension obtained from the step (a).

13. A kit for preparing nanocomplexes according to claim 1, said kit comprising
  at least one vessel with a solution of a bisphosphonate or the bisphosphonate in solid form;
  at least one vessel with a suspension of inorganic nanovectors;
  at least one vessel containing a suspension containing stealth lipid nanovectors.

14. The kit according to claim 13 wherein the suspension containing the stealth lipid nanovectors contains also a ligand for receptors overexpressed by cancer cells or the kit further comprises at least one vessel containing the ligand as powder or in aqueous solution.

15. The nanocomplex according to claim 7, wherein the lipid mixture comprises one or more of the group consisting of 1,2-dioleoyl-3-trimethylammonium-propane chloride (DOTAP), cholesterol, 1,2-diacyl-sn-glycerol-3-phosphoethanolamine-N-[methoxy(polyethylene glycol)-2000] (DSPE-PEG 2000).

* * * * *